(12) United States Patent  (10) Patent No.: US 7,430,982 B2
Koivukunnas et al.  (45) Date of Patent: Oct. 7, 2008

(54) PRINTED TTI INDICATORS

(75) Inventors: Pekka Koivukunnas, Jarvenpaa (FI); Eero Hurme, Espoo (FI)

(73) Assignee: Avantone Oy, Tampere (FI)

( * ) Notice: Subject to any disclaimer, the term of this patent is extended or adjusted under 35 U.S.C. 154(b) by 0 days.

(21) Appl. No.: 10/545,815

(22) PCT Filed: Feb. 25, 2004

(86) PCT No.: PCT/FI2004/000096

§ 371 (c)(1),
(2), (4) Date: Aug. 16, 2005

(87) PCT Pub. No.: WO2004/077001

PCT Pub. Date: Sep. 10, 2004

(65) Prior Publication Data

US 2006/0130734 A1  Jun. 22, 2006

(30) Foreign Application Priority Data

Feb. 27, 2003  (FI)  .................................. 20030298

(51) Int. Cl.
*G01K 11/00* (2006.01)
*G01K 11/12* (2006.01)
(52) U.S. Cl. .................. 116/219; 116/207; 374/162
(58) Field of Classification Search ................. 116/216, 116/206, 201, 207, 247, 219; 374/106, 162; 206/459.1
See application file for complete search history.

(56) References Cited

U.S. PATENT DOCUMENTS

| | | | | | |
|---|---|---|---|---|---|
| 2,971,852 | A | * | 2/1961 | Schulein ..................... | 116/217 |
| 3,093,242 | A | * | 6/1963 | Huyck et al. ................ | 206/210 |
| 3,822,189 | A | * | 7/1974 | Tornmarck .................. | 435/12 |
| 3,963,442 | A | * | 6/1976 | Bullard et al. .............. | 436/165 |
| 3,967,579 | A | * | 7/1976 | Seiter ......................... | 116/219 |
| 4,022,149 | A | * | 5/1977 | Berger ........................ | 116/219 |
| 4,057,029 | A | | 11/1977 | Seiter | |
| 4,154,107 | A | * | 5/1979 | Giezen et al. ................ | 116/207 |
| RE30,267 | E | * | 5/1980 | Bruschi ...................... | 436/170 |
| 4,280,441 | A | * | 7/1981 | McNeely .................... | 116/219 |
| 4,382,700 | A | * | 5/1983 | Youngren ................... | 116/216 |
| 4,390,291 | A | * | 6/1983 | Gaven et al. ................ | 116/217 |
| 4,408,557 | A | * | 10/1983 | Bradley et al. .............. | 116/206 |
| 4,410,493 | A | | 10/1983 | Joslyn | |
| 4,729,671 | A | * | 3/1988 | Asano et al. ................ | 116/219 |
| 4,972,953 | A | * | 11/1990 | Friedman et al. ......... | 206/459.1 |
| 5,053,339 | A | | 10/1991 | Patel | |
| 5,254,473 | A | | 10/1993 | Patel | |
| 5,325,721 | A | * | 7/1994 | Pendergrass, Jr. .......... | 116/216 |
| 5,476,792 | A | | 12/1995 | Ezrielev et al. | |

(Continued)

FOREIGN PATENT DOCUMENTS

EP  0 484 578 A1  5/1992

(Continued)

*Primary Examiner*—R. A. Smith
(74) *Attorney, Agent, or Firm*—Oliff & Berridge, PLC

(57) ABSTRACT

The present invention relates to time-temperature integrating indicators, also known as TTI indicators, which are easily printable on substrates, such as packaging materials, and to a method for the manufacture of packaging materials comprising printed TTI indicators. The printed TTI indicator is selectively activated at the time of packaging of a perishable product or alternatively at the time of opening of the package of a perishable product.

27 Claims, 1 Drawing Sheet

U.S. PATENT DOCUMENTS

Figure 1:
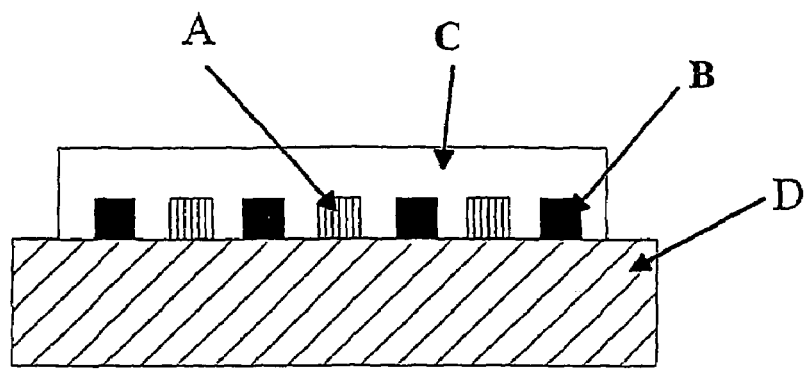

| | | | | |
|---|---|---|---|---|
| 5,667,303 A | * | 9/1997 | Arens et al. | 116/219 |
| 5,756,356 A | | 5/1998 | Yanagi et al. | |
| 5,797,344 A | * | 8/1998 | Ramsey et al. | 116/206 |
| 6,103,351 A | * | 8/2000 | Ram et al. | 116/219 |
| 6,667,092 B1 | * | 12/2003 | Brollier et al. | 428/182 |
| 7,036,452 B1 | * | 5/2006 | Tester | 116/207 |
| 2003/0199095 A1 | * | 10/2003 | Yuyama et al. | 436/1 |

FOREIGN PATENT DOCUMENTS

| | | |
|---|---|---|
| EP | 0 735 368 A1 | 10/1996 |
| EP | 0 930 489 A2 | 7/1999 |
| EP | 1 048 477 A1 | 11/2000 |

\* cited by examiner

PRINTED TTI INDICATORS

FIELD OF THE INVENTION

The present invention relates to time-temperature integrating indicators, also known as TTI indicators, which are easily printable on substrates, such as packaging materials, and to a method for the manufacture of packaging materials comprising printed TTI indicators. The printed TTI indicator is selectively activated at the time of packaging of a perishable product or alternatively at the time of opening of the package of a perishable product.

STATE OF THE ART

Colour-changing or colour-forming temperature sensitive indicators for monitoring of handling of perishable goods are well known in the art. Such perishable goods are for example foodstuffs, pharmaceuticals, biological materials, chemical substances, coating compositions, adhesives, cosmetics, food additives, photographic supplies and vaccines. There is a growing interest for indicator systems and devices for monitoring a temperature and a time as an accumulated value of articles, which are stored at a constant temperature for a certain period of time. Particularly such indicator systems are used for signaling when the articles have reached the point of quality loss or unsafe condition due to excessive temperature exposures.

Several time-temperature integrating indicator systems and devices have been proposed. Usually they are either attached as adhesive labels to the surface of consumer packages of perishable goods or incorporated onto the packages at the time of production of the goods to show when a package has been temperature abused or has reached the end of its useful shelf life. Most of the TTIs available are colourimetic labels, which respond to cumulative exposure to time and temperature.

TTIs typically provide a visual indicator that gradually changes with time faster at elevated temperatures and slower at colder temperatures. Commercially available are products, which employ enzymatic colour indicators to show the amount of higher temperature exposure of a stored or shipped temperature-sensitive commodity. The enzyme indicator is activated at the beginning of a monitoring period by applying pressure on a plastic bubble strip thus releasing the enzyme, substrate and indicator to react with each other. Another indicator system is based on a polymerisation reaction and the system must be stored frozen prior to usage. Also a product based on a dyed wax that diffuses along a strip of paper is known.

An improved indicator system utilising the concept of two different indicator technologies is disclosed in EP 0 484 578. This indicator device comprises a system of printable multi-layer compatible composition with an independently acting integrating indicator and another threshold indicator. In a preferable embodiment, diacetylenic monomers are printed on a transparent film as the primary indicia of long-term storage. As a function of time and temperature, the material gradually and irreversibly develops colour. The secondary indicator is set to trigger at a pre-determined temperature very rapidly. The combined indicator device yields a single output.

U.S. Pat. No. 5,756,356 discloses an indicator material and a method of indicating a time or a temperature time accumulated value as a colour change which comprises providing an oxidation-polymerizable dyestuff (agent A) and oxidising agent (agent B) in a non-contact state and the agent A and/or the agent B being held in a carrier which may be a resin or liquid media. When activation takes place, A and B are brought into contact with each other. In said indicator material, between a first layer containing agent A in a carrier and a second layer containing agent B in a carrier, there is a third layer so-called spacing layer which may include woven fabric, non-woven fabric, powder and micro-capsules. The indicator material may be obtained by a printing method using as a carrier a source marking ink, such as gravure ink, offset ink, screen ink, a lithographic ink or flexographic ink, or by a printing method using an on-demand ink, such as stamp ink, carbon-free paper ink, inkjet ink, wire dot ink, typewriter ink or thermal ink. A layer containing the agent B may be directly formed on the surface of a tape-shaped layer containing the agent A by printing method just before initiation of the measurement of the temperature time accumulated value. A layer containing the agent A may be formed on a transparent substrate by a printing method and the resultant laminate may be attached to a surface over tape-shaped layer containing the agent A just before the initiation and a measurement of a temperature-time accumulated value. A layer containing the agent A and a layer containing the agent B may be formed on a transparent film by any one of a silk screen printing method, a gravure printing method and an offset printing method. However, control of the reaction rate of an oxidation reaction may cause difficulties and the colour change may not be sufficiently fast.

A recording material is provided in EP 1048477, which material is suitable for use in a direct thermal imaging apparatus and which contains at least one indicator compound that is convertible from an inactive state to an active state by the application of heat with a direct thermal imaging apparatus. The recording material refers to any substrate that is suitable for use in a thermal imaging apparatus and it may take the form of an article or product packaging such as a cardboard container or a label. Substrates may include all types of paper, both thermal paper and non-thermal paper or adhesive labels. Preferred indicator compounds are kinetic indicator compounds, which provide a change in colour from a chemical reaction in response to the exposure element of interest such as integrated time and temperature. It may be convenient to apply the indicator composition in the form of a printed message on the recording material or alternatively, the layer of the indicator compound on the recording material can be activated in the form of a printed message. This method requires always the use of a thermal imaging apparatus.

WO 01/64430 discloses an indicator system, which is attached to a unit of thermally sensitive perishable product and is activated at a time of introduction of the unit into commerce to initiate the monitoring of the unit's cumulative exposure to harmful temperatures. Said indicator system comprises use of a direct self-adhesive thermal label paper comprising a colour-forming high-temperature printing composition, and a second activating element component in the form of a self-adhesive tab or label comprising a substrate, an adhesive composition and an activating component that, when applied to the direct thermal coating, combines with the primary composition to enable its colour-forming reaction. The application of the second element may also be performed directly in fluid form using clear ink comprising an activating component.

An indicator device for use in steam sterilization is disclosed in U.S. Pat. No. 4,410,493. Said device consists of a permeable wick material which is treated with a suitable indicator chemical such as sebacic acid, to provide an indication like colour change when exposed to certain constituents in an environment. The wick is sealed between two layers of an impermeable material and the device may contain a backing material of polymeric material or metal foil.

Several activatable time-temperature indicator systems have been proposed. Most of the systems involve a complicated indicator system or a label which is to be affixed to a perishable product and often co-reactant components are in close proximity but yet maintaining reactive isolation by means of additional intervening layers, encapsulating films and the like. Such TTI systems and devices are often costly to manufacture, complicated to activate and they are prone to inadvertent premature activation. Additionally, adhesive labels tend to be released from the articles. Based on the above it can be realised that there exists a need for a low cost and reliable time-temperature indicator, which is directly printable on the packaging material, which can be cost effectively manufactured and easily activated and no affixing of labels or use of any additional equipment is required.

OBJECT OF THE INVENTION

An object of the present invention is a TTI indicator, which can be directly printed on a substrate material and which can be activated at a desired moment by printing, or alternatively a TTI indicator, which can be printed between layers of a substrate material, and which can be activated at a desired moment by opening of a package containing the indicator. Said TTI indicator provides a rapid and clear indication of expiration.

A further object of the invention is a method for the manufacture of TTI indicator, which can be directly printed on a substrate material and which can be activated at a desired moment by printing, or alternatively a TTI indicator, which can be printed between layers of a substrate material, and which can be activated at a desired moment by opening of a package containing the indicator, and which indicator provides a rapid and clear indication of expiration.

A further object of the invention is a method for the monitoring a temperature and a time as an accumulated value of a perishable product with the TTI indicator according to the invention, either from the time of packaging of the perishable product or in the alternative embodiment, from the time of opening of the package of the perishable product.

The characteristic features of the printed TTI indicator, of the method for the manufacture of a printed TTI indicator and of the method for the monitoring a temperature and a time as an accumulated value of a perishable product with the TTI indicator according to the invention are provided in the claims.

SUMMARY OF THE INVENTION

It has now been realised that a TTI indicator can be easily manufactured directly on a substrate in connection with printing of the substrate, and suitably at the time of packaging of the final product, which is to be monitored. Thus the time of printing is the time of activation.

In an alternative embodiment the TTI may be printed between layers of a substrate material. At the time of packaging of the final product or at the time of the manufacture of the packaging material/substrate the TTI indicator may be printed on the inner side of the packaging material and it is then sealed between packaging material/substrate layers. The TTI is activated at a desired moment by opening of a package, containing the indicator, of the perishable product.

The TTI indicator according to the invention comprises a substrate, an optional protective layer on the substrate, a diffusion layer, agent A and agent B on the substrate or on the protective layer or on the diffusion layer, and an optional outer protective layer. In the first embodiment agent A and agent B are adjacent to each other but not in direct contact with each other. In the alternative embodiment agent A and agent B are in direct contact with each other and either adjacent to each other, on the top of each other or blended together.

DETAILED DESCRIPTION OF THE INVENTION

It has been noted that many of the problems and disadvantages related to the solutions according to the prior art can be avoided or at least substantially decreased by the TTI according to the invention. A TTI indicator can be easily manufactured directly on a substrate in connection with printing of the substrate, and suitably at the time of packaging of the final product, which is to be monitored. The time of printing of the TTI indicator is the time of activation of the TTI indicator.

In the alternative embodiment the TTI may be printed between layers of a substrate material. At the time of packaging of the final product or at the time of the manufacture of the packaging material/substrate the TTI indicator may suitably be printed on the inner side of the packaging material and it is then sealed between packaging material/substrate layers. The TTI is activated at a desired moment by opening of a package, containing the indicator, of the perishable product.

The TTI indicator according to the first embodiment of the invention comprises a substrate, an optional protective layer on the substrate, a diffusion layer, at least one stripe or dot or a geometrical figure comprising agent A and at least one stripe or dot or a geometrical figure comprising agent B, adjacent to each other but not in direct contact with each other, on the substrate or on the protective layer or on the diffusion layer, and an optional outer protective layer.

The TTI indicator according to the alternative embodiment of the invention comprises a substrate, an optional protective layer on the substrate, a diffusion layer, at least one stripe or dot or a geometrical figure comprising agent A and at least one stripe or dot or a geometrical figure comprising agent B, in direct contact with each other and either adjacent to each other, on the top of each other or blended together, on the substrate or on the protective layer or on the diffusion layer, and an optional outer protective layer and an outer substrate layer.

Figure 2:
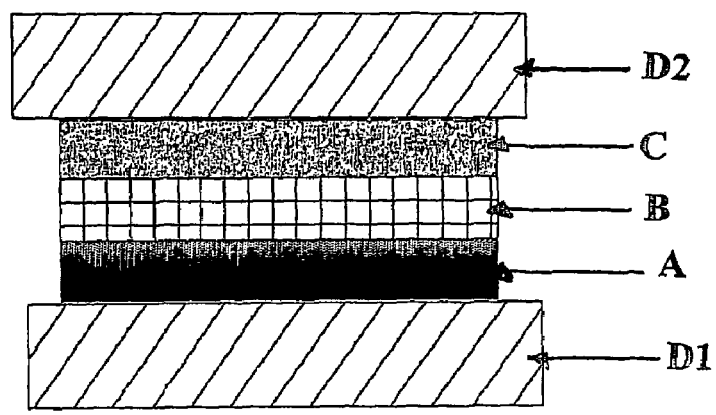
Figure 3:
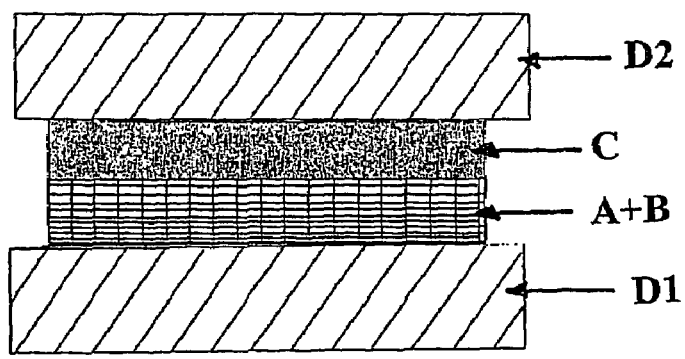

The invention is illustrated in more detail with enclosed FIGS. 1-3:

FIG. 1. A TTI indicator according to the first embodiment of the invention with a diffusion layer C on the agents A and B.

FIG. 2. A TTI indicator according to the alternative embodiment of the invention with a diffusion layer C on the agents A and B, which are on top of each other.

FIG. 3. Another TTI indicator according to the alternative embodiment of the invention with a diffusion layer C on the agents A and B, which are blended together.

In FIG. 1 a TTI indicator according to the invention is presented. Agents A and B are printed on a substrate D (which is optionally coated with a protective layer) as stripes, dots or geometrical figures, adjacent to each other but not in direct contact with each other. On the agents A and B a diffusion layer C is printed, which may optionally be coated with a protective layer.

In FIG. 2 a TTI indicator according to the alternative embodiment of the invention is presented. Agents A and B are printed on a inner substrate layer D1 (which is optionally coated with a protective layer) as stripes, dots or geometrical figures, on top of each and in direct contact with each other.

On the agents A and B a diffusion layer C is printed, which may optionally be coated with a protective layer. The indicator is covered the outer substrate layer D2 (which is optionally coated with a protective layer), which may comprise same or different material as the inner substrate layer D1.

In FIG. 3 another TTI indicator according to the alternative embodiment of the invention is presented. A blend of agents A and B is printed on a inner substrate layer D1 (which is optionally coated with a protective layer) as stripes, dots or geometrical figures. On the blended agents A and B a diffusion layer C is printed, which may optionally be coated with a protective layer. The indicator is covered the outer substrate layer D2 (which is optionally coated with a protective layer), which may comprise same or different material as the inner substrate layer D1.

According to one embodiment of the invention, on the substrate or optionally on the protective layer, which is situated on the substrate, a diffusion layer is applied, suitably by offset, inkjet, flexo, silkscreen, gravure, folio or spray printing and a particularly suitable printing method is a digitally controlled printing inkjet method. The substrate containing the diffusion layer and optional protective layer may then be stored in a warehouse etc until the final product is packed in it. In the first embodiment, in connection with the manufacture of the final package containing the product the agents A and B and the optional outer protective layer are applied by printing on the diffusion layer and the activation of the indicator takes place.

According to another embodiment of the invention, the agents A and B, the diffusion layer and optionally the protective layer(s) are all applied by printing on the substrate or on the protective layer in connection with the manufacture of the final package containing the product and the activation of the indicator takes place. A suitable printing method is offset, inkjet, flexo, silkscreen, gravure, folio or spray printing, preferably inkjet, and particularly preferably a digitally controlled inkjet printing method is used.

In the first embodiment the activation of the TTI indicator is performed by printing agent A and agent B in connection with packaging of goods to be monitored. Agents A and B may be printed in the form stripes or dots or geometrical figures, and the like. All conventional graphics, including barcodes, required for the indicator may be printed simultaneously.

In the alternative embodiment the TTI indicator is printed between the packaging material/substrate layers and it is activated by opening the package, particularly by tearing the packaging material containing the TTI indicator between the packaging material and thus revealing the indicator and exposing it to the surrounding atmosphere. The agent B is preferable an easily evaporating organic acid in this embodiment.

In another embodiment a combination of TTI indicator and an additional temperature indicator is printed on the substrate/packaging.

The substrate is selected from packaging material, which may comprise paper, cardboard, plastic foil, metal or glass, preferably paper, cardboard or plastic foil.

The substrate may optionally comprise a protective layer, which is any transparent material with good water vapour barrier properties. Suitable ones are polyolefins as well as aqueous and solvent containing laquers. Preferably polyethylene, polypropylene and acrylic based lacquers are used. The protective layer is applied onto the substrate by a suitable coating or printing method known to a man skilled in the art, such as spray coating, laminating or offset, inkjet, flexo, silkscreen, gravure, folio or spray printing, a preferable printing method is a digitally controlled inkjet printing method. The protective layer may also be applied on the TTI as an outer protective layer to prevent agents A and B from drying.

The diffusion layer is a membrane comprising film-forming substances selected from cellulose derivatives such as carboxy methyl cellulose, micro-crystalline cellulose, methyl cellulose, hydroxypropyl methyl cellulose, starches, corn protein (Zein protein), soy protein, casein, glutein, cyclodextrins, cithosan, lecithin and phospholipide, hydro-gels and sol-gels, gum arabic, agarose and resins, dissolved in a solvent or mixture of solvents. Suitable solvents are water, alcohols such as ethanol and glycols, such as polyethylene glycol.

Also additives selected from lauric acid, cinnamic aldehyde, eugenol, beeswax and acetylated monoglyseride may be used for adjusting the diffusion rate in the diffusion layer.

The thickness and density of the diffusion layer can be varied depending of the desired diffusion rate, which corresponds to the maximum time factor.

The indicator comprises agent A and agent B which, when brought into contact with each other react and yield a by visual light and/or UV-light detectable change of colour. In the alternative embodiment the agent A and agent B are in direct contact with each other at the time of activation and the original colour of agent A returns when agent B is evaporated from the layer or mixture. This change of colour is equally detectable by visual light and/or UV-light.

In the following table 1 suitable pH-ranges and colour changes of some suitable pH-indicators for the present invention are disclosed.

TABLE 1

| Substance | Colour change | Colour change pH range |
| --- | --- | --- |
| Thymol blue | Red-yellow | 1.2-2.8 |
| Methyl orange | Red-orange | 3.1-4.4 |
| Methyl red | Red-yellow | 4.4-6.2 |
| Lithmus | Red-blue | 5.0-8.0 |
| Bromthymol blue | Yellow-blue | 6.0-7.6 |
| Phenol phthalein | Colourless-red | 8.2-9.8 |
| Thymol phthalein | Colourless-blue | 9.3-10.5 |

Agent A is a pH-indicator also called a pH-dye. The pH-indicator is preferably selected from the group consisting of methyl red, cresol red, bromthymol blue, neutral red, phenol phthalein, bromocresol red, bromocresol green, bromocresol blue, xylenol blue, thymol blue, methyl orange, lithmus and thymol phthalein, particularly preferably bromocresol blue. Agent A may also contain a solvent, suitably water or alcohol, such as ethanol or a mixture thereof, and/or a humectant, suitably a glycol, such as polyethylene glycol, to prevent drying of the composition on the print head during printing operation.

Agent B is a material with adjusted pH, preferably an organic acid selected from citric acid, tartaric acid, lactic acid, acetic acid or formic acid, preferably citric acid. Agent B may also contain a solvent, suitably water or alcohol, such as ethanol or a mixture thereof, and/or a humectant, suitably a glycol, such as polyethylene glycol, to prevent drying of the composition on the print head during printing operation.

Thus the TTI indicator according to the first embodiment is activated at the time of packaging of the articles in the substrate material having optionally the printed diffusion layer on its' surface or on the protective layer, by applying by printing the agents A and B. A suitable printing method is inkjet, offset, flexo, silkscreen, gravure, folio or spray printing, preferably inkjet.

Agent A and agent B are preferably incorporated in a carrier, suitably in a printing ink composition. A printing ink composition comprises:

- 10-20 wt-% of agent A or of agent B, or a blend thereof in the alternative embodiment;
- 50-70 wt-% of a water-miscible or water soluble solvent, such as an alcohol like ethanol, toluene, xylene, or mixtures thereof;
- binder selected from oils, resins, nitrocellulose, polyamides and acrylates; and
- additive or combination of additives selected from plasticizers, waxes, anti-foam substances, antioxidants, humectants and fillers.

The printing ink composition has low viscosity, it dries rapidly and it is non-tixotropic.

According to the first embodiment of the invention one or more stripes or dots or geometrical figures comprising agents A and B may be printed on the substrate and the distance between the A and B stripes or dots or figures can adjusted to achieve the reaction at a desired point of time. Agent A and agent B migrate in the diffusion layer towards each other. The reaction between agent A and agent B takes place at a predetermined moment of time and it provides a rapid and clear indication of expiration. The diffusion can also be influenced by the selection of a suitable pH-indicator (ph-dye) and material with adjusted pH, such as an organic acid. Suitable printing methods are inkjet, offset, flexo, silkscreen, gravure, folio or spray printing, preferably digitally controllable inkjet printing methods.

The properties of the TTI indicator may be adjusted by a choice of the reactive components A and B and also by the amount of the compounds used. The amounts may easily be adjusted by changing the gravure figures in printing, the cell size, and the viscosity or dry/solid content of the printing ink.

Because the printing may be carried out just before or at the time of packaging of the product, this makes it possible to rapidly and specificly for each product to change the time-temperature sensitivity.

The present invention comprises a TTI indicator which is printed on a substrate such as cardboard or paper, useful as packaging material for perishable goods and activated by printing the indicator at the time of packaging and releasing of the goods on the market. Said printed indicator is useful for monitoring the exposure of a perishable foodstuff or a commodity product to a critical condition of such time and temperature which will result in spoilage or unacceptable degradation of the quality of the perishable product.

In the alternative embodiment the TTI indicator is printed between the packaging material/substrate layers and it is activated by opening the package, particularly by tearing the packaging material containing the TTI indicator between the packaging material and thus revealing the indicator and exposing it to the surrounding atmosphere. This embodiment is particularly suitable for monitoring of the time and temperature, which will result in spoilage or unacceptable degradation of the quality of a perishable product after opening of the package. The easily evaporating agent B is released from the TTI indicator, resulting in a change of colour.

Perishable products include foodstuffs such as meat, fish, poultry, plants and the like, food additives, biological materials, drugs, cosmetics, photographic supplies, coating compositions, adhesives, vaccines, implantation related organs and chemical substances.

Visible light or humidity in the surroundings has no effect on the reaction between agents A and B.

The parameters and the sensitivity of the reaction can be easily adjusted, even during the manufacturing process. The content of the printed information can be changed in-line during the printing process. The process according to the invention allows the production of TTI indicators, which perform in a controlled and reliable manner and which provide a rapid and clear indication of expiration.

The present invention provides a cost effective printed TTI indicator on a substrate or between the substrate, it is easy to use, environmentally acceptable as the indicator is printed directly on substrate, it is not much labour consuming as no affixing of labels is needed. Further, as different products have different temperature/time limits and expiration times and earlier several different types of indicator labels were needed, the present invention provides a method which yields indicators for different products by adjusting in-line the amounts of each component, the distances of stripes or dots or figures of agents A and B, by using a digitally controllable printing method for the printing of the ingredients of the indicator. The components are also suitable for the use in food products.

The invention claimed is:

1. A TTI indicator device comprising:
   a substrate layer selected from packaging materials comprising paper, cardboard, plastic foil, metal or glass; agent A and agent B, a diffusion layer comprising film-forming substance(s) selected from carboxymethyl cellulose, micro-crystalline cellulose, methyl cellulose, hydroxypropylmethyl cellulose, starches, corn protein, soy protein, casein, glutein, cyclodextrins, cithosan, lecithin, phospholipide, hydro-gels, sol-gels, gum Arabic and agarose dissolved in a solvent or mixture of solvents, agent A being a pH-indicator and agent B being an organic acid selected from citric acid, tartaric acid, lactic acid, acetic acid and formic acid, and
   a) the agent A and agent B being adjacent to each other but not in direct contact with each other and the diffusion layer being on the agent A and agent B, or
   b) the agent A being on top of agent B and the diffusion layer being on the agent A, or the agent B being on top of the agent A and the diffusion layer being on the agent B; or
   c) a blend of the agents A and B being on the substrate layer and the diffusion layer being on the blend.

2. The TTI indicator device according to claim 1, wherein the substrate layer comprises a protective layer and the agent A and agent B being on the protective layer.

3. The TTI indicator device according to claim 1, wherein the diffusion layer comprises a protective layer thereon.

4. The TTI indicator device according to claim 1, wherein in alternatives b) and c) the TTI indicator comprises an outer substrate layer on the diffusion layer.

5. The TTI indicator device according to claim 4, wherein the TTI indicator is activatable at a desired moment by opening of a package containing the indicator.

6. The TTI indicator device according to claim 4, wherein the TTI indicator comprises a protective layer on the outer substrate layer.

7. The TTI indicator device according to claim 1, wherein the TTI indicator is activatable at a desired moment by printing of the indicator.

8. The TTI indicator device according to claim 1, wherein the protective layer is selected from polyolefins and lacquers, preferably the protective layer comprises polyethylene, polypropylene or acrylic based lacquer.

9. The TTI indicator device according to claim 1, wherein the solvents are selected from water, alcohols and glycols.

10. The TTI indicator device according to claim 1, wherein the agent A is selected from the group consisting of methyl red, cresol red, bromthymol blue, neutral red, phenol phthalein, bromocresol red, bromocresol green, bromocresol blue, xylenol blue, thymol blue, methyl orange, lithmus and thymol phthalein, preferably bromocresol blue.

11. The TTI indicator device according to claim 1, wherein the agent A contains a solvent or a mixture thereof and/or a humectant.

12. The TTI indicator device according to claim 1, wherein the agent B contains a solvent or a mixture thereof and/or a humectant.

13. A method of monitoring the exposure of a perishable product to a critical condition of such time and temperature which will result in spoilage or unacceptable degradation of the quality of the perishable product using the TTI indicator according to claim 1.

14. The monitoring method according to claim 13, wherein the perishable products include foodstuffs, food additives, biological materials, drugs, cosmetics, photographic supplies, coating compositions, adhesives, vaccines, implantation related organs and chemical substances.

15. A method for the manufacture of a TTI indicator device, wherein at least one stripe or dot or a geometrical figure comprising agent A and at least one stripe or dot or a geometrical figure comprising agent B are printed on a substrate layer, whereon either or both agent A and agent B a diffusion layer is provided, the diffusion layer being printed, the substrate layer being selected from packaging materials comprising paper, cardboard, plastic foil, metal or glass, the diffusion layer comprising film-forming substance(s) selected from carboxymethyl cellulose, micro-crystalline cellulose, methyl cellulose, hydroxypropylmethyl cellulose, starches, corn protein, soy protein, casein, glutein, cyclodextrins, cithosan, lecithin, phospholipide, hydro-gels, sol-gels, gum Arabic and agarose, dissolved in a solvent or mixture of solvents, the agent A being pH-indicator and the agent B being an organic acid selected from citric acid, tartaric acid, lactic acid, acetic acid and formic acid; and the at least one stripe or dot or a geometrical figure comprising the agent A and the at least one stripe or dot or a geometrical figure comprising the agent B are printed adjacent to each other but not in direct contact with each other; or at least one stripe or dot or a geometrical figure comprising the agent A and at least one stripe or dot or a geometrical figure comprising the agent B, one of either agent A or agent B being arranged on top of the other, are printed on top of each other on the substrate layer; or at least one stripe or dot or a geometrical figure comprising a blend of the agent A and the agent B is printed on the substrate layer.

16. The method according to claim 15 for the manufacture of a TTI indicator device, wherein a protective layer is printed on the substrate layer and the agent A and the agent B, one of either agent A or agent B being arranged on top of the other, are printed on the substrate comprising the protective layer.

17. The method according to claim 15 for the manufacture of a TTI indicator device, wherein a protective layer is printed on the diffusion layer.

18. The method according to claim 17 for the manufacture of a TTI indicator device, wherein the diffusion layer or diffusion layer printed with the protective layer is covered with an outer surface layer.

19. The method according to claim 18 for the manufacture of a TTI indicator device, wherein on the outer surface layer a protective layer is printed.

20. The method according to claim 15 for the manufacture of a TTI indicator device, wherein inkjet, offset, flexo, silkscreen, gravure, folio or spray printing is used for printing.

21. The method according to claim 15 for the manufacture of a TTI indicator device, wherein the protective layer is selected from polyolefins and lacquers, preferably the protective layer comprises polyethylene, polypropylene or acrylic based lacquer.

22. The method according to claim 15 for the manufacture of a TTI indicator device, wherein the solvents are selected from water, alcohols and glycols.

23. The method according to claim 15 for the manufacture of a TTI indicator device, wherein the agent A is selected from the group consisting of methyl red, cresol red, bromthymol blue, neutral red, phenol phthalein, bromocresol red, bromocresol green, bromocresol blue, xylenol blue, thymol blue, methyl orange, lithmus and thymol phthalein, preferably bromocresol blue.

24. The method according to claim 15 for the manufacture of a TTI indicator device, wherein the agent A contains a solvent or a mixture thereof and/or a humectant.

25. The method according to claim 15 for the manufacture of a TTI indicator device, wherein the agent B contains solvent or a mixture thereof and/or a humectant.

26. The method according to claim 15 for the manufacture of a TTI indicator device, wherein the agent A and the agent B are incorporated each or the agent A and the agent B as a blend, in a carrier, preferably in a printing ink composition.

27. The method according to claim 26 for the manufacture of a TTI indicator device, wherein the printing ink composition comprises:
10-20 wt-% of the agent A or the agent B or a blend thereof;
50-70 wt-% of the water-miscible or water-soluble solvent or mixtures thereof;
a binder selected from oils, resins, nitrocellulose, polyamides and acrylates; and
an addictive or combination of addictives selected from plasticizers, waxes, anti-foam substances, antioxidants humectants and fillers.

* * * * *